United States Patent
Gomez et al.

(10) Patent No.: US 7,534,258 B2
(45) Date of Patent: *May 19, 2009

(54) INTRAVASCULAR STENT

(75) Inventors: Andreina P. Gomez, Santa Clara, CA (US); Diem Uyen Ta, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/217,213

(22) Filed: Aug. 31, 2005

(65) Prior Publication Data

US 2006/0052860 A1  Mar. 9, 2006

Related U.S. Application Data

(63) Continuation of application No. 10/695,290, filed on Oct. 27, 2003, now Pat. No. 6,939,373, which is a continuation of application No. 10/645,265, filed on Aug. 20, 2003, now Pat. No. 6,929,657, which is a continuation of application No. 09/879,263, filed on Jun. 11, 2001, now Pat. No. 6,629,994.

(51) Int. Cl.
*A61F 2/90* (2006.01)

(52) U.S. Cl. .................................. 623/1.17; 623/1.15

(58) Field of Classification Search ................ 623/1.15, 623/1.16, 1.17, 1.18, 1.19, 1.2, 1.21, 1.22
See application file for complete search history.

(56) References Cited

U.S. PATENT DOCUMENTS

| 5,992,000 | A | 11/1999 | Humphrey et al. | |
|---|---|---|---|---|
| 6,108,886 | A | 8/2000 | Kimes et al. | |
| 6,264,688 | B1 | 7/2001 | Herklotz et al. | |
| 6,325,826 | B1 * | 12/2001 | Vardi et al. | 623/1.35 |
| 6,330,884 | B1 | 12/2001 | Kim | |
| 6,497,723 | B1 | 12/2002 | Starck et al. | |
| 6,540,775 | B1 | 4/2003 | Fischell et al. | |
| 6,616,689 | B1 * | 9/2003 | Ainsworth et al. | 623/1.16 |
| 6,618,921 | B1 | 9/2003 | Thornton | |
| 6,629,994 | B2 * | 10/2003 | Gomez et al. | 623/1.15 |
| 6,656,220 | B1 * | 12/2003 | Gomez et al. | 623/1.15 |
| 6,740,114 | B2 * | 5/2004 | Burgermeister | 623/1.17 |
| 6,929,657 | B2 * | 8/2005 | Gomez et al. | 623/1.11 |

(Continued)

FOREIGN PATENT DOCUMENTS

JP  505441/1999  5/1999

(Continued)

*Primary Examiner*—Thomas J Sweet
(74) *Attorney, Agent, or Firm*—Fulwider Patton LLP

(57) ABSTRACT

The invention is directed to an expandable stent for implanting in a body lumen, such as a coronary artery, peripheral artery, or other body lumen. The invention provides for an intravascular stent having a plurality of cylindrical rings connected by undulating links. The stent has a high degree of flexibility in the longitudinal direction, yet has adequate vessel wall coverage and radial strength sufficient to hold open an artery or other body lumen. The stent can be compressed or crimped onto a catheter to a very low profile since the peaks that are adjacent the curved portion of the undulating link are shorter than other peaks in the same cylindrical ring to prevent overlap yet still achieve a very low profile, tightly crimped stent onto a catheter.

9 Claims, 15 Drawing Sheets

U.S. PATENT DOCUMENTS 6,969,373 B2 * 11/2005 Schwartz et al. ....... 604/170.03
2002/0121497 A1 9/2002 Tomonto

FOREIGN PATENT DOCUMENTS

| JP | 2000-316983 | 11/2000 |
| JP | 2001-112873 | 4/2001 |
| WO | WO 99/62430 A1 | 12/1999 |
| WO | WO 01/00112 A1 | 1/2001 |
| WO | WO 01/21095 A2 | 3/2001 |

* cited by examiner

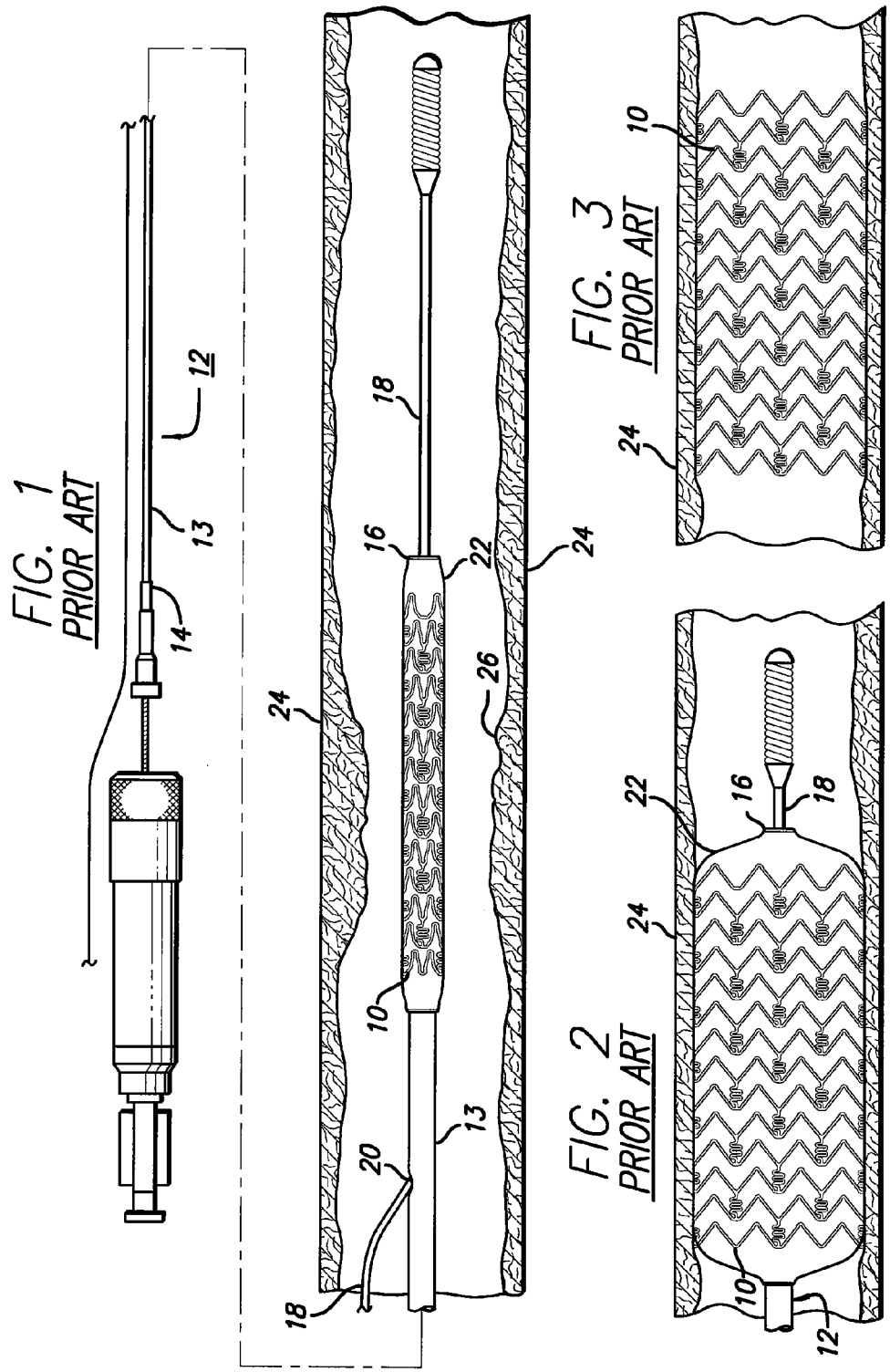

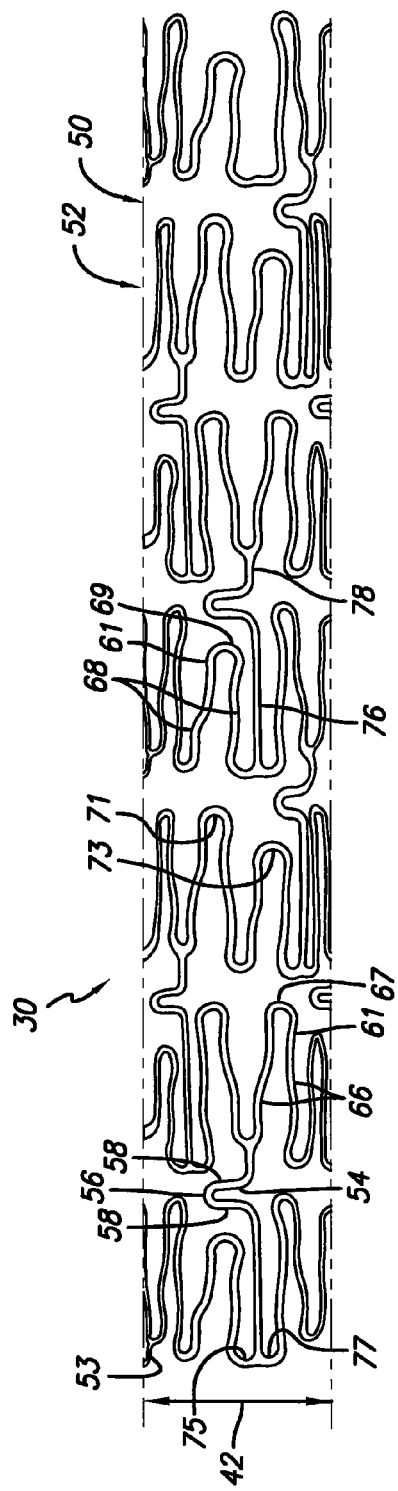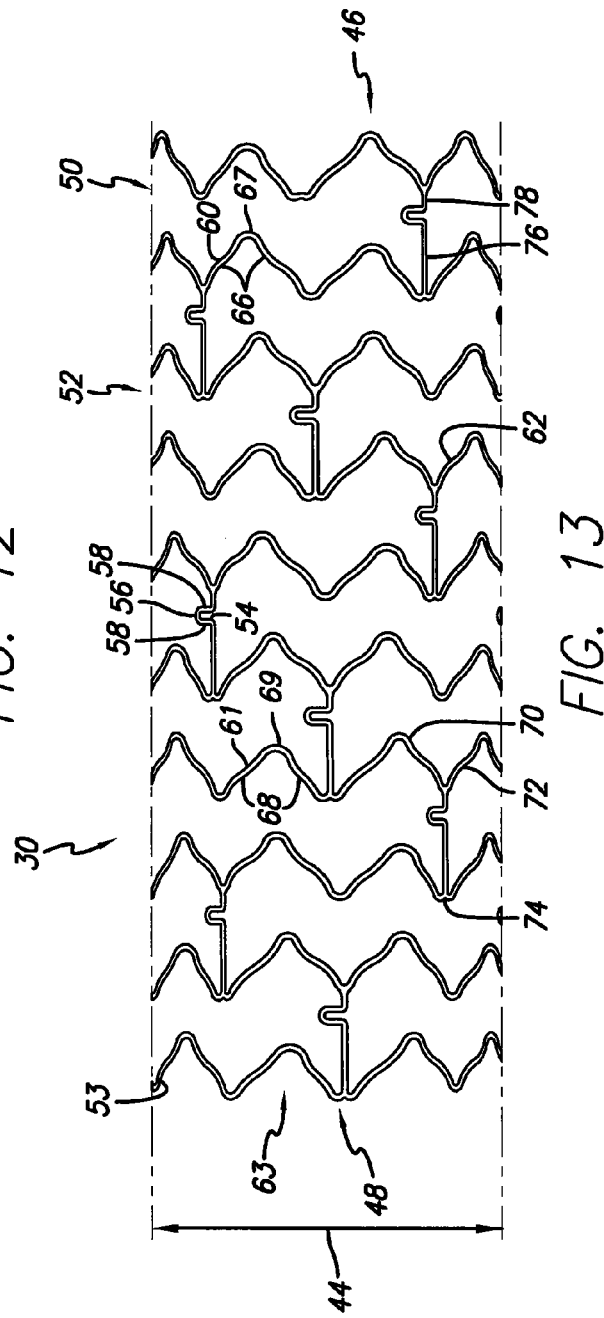

INTRAVASCULAR STENT

This is a continuation application of U.S. Ser. No. 10/695,290 filed Oct. 27, 2003 which will issue as U.S. Pat. No. 6,939,373 on Sep. 6, 2005, which is a continuation of U.S. Ser. No. 10/645,265 filed Aug. 20, 2003 which issued as U.S. Pat. No. 6,929,657 on Aug. 16, 2005, which is a continuation of U.S. Ser. No. 09/879,263 filed Jun. 11, 2001 now U.S. Pat. No. 6,629,994 issued Oct. 7, 2003. Applicant claims priority to each application in the chain. Each of the foregoing applications is incorporated herein by reference thereto.

BACKGROUND OF THE INVENTION

The invention relates to vascular repair devices, and in particular intravascular stents, which are adapted to be implanted into a patient's body lumen, such as a blood vessel or coronary artery, to maintain the patency thereof Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, the prior art stents depicted in FIGS. 1-5 have multiplex cylindrical rings connected by one or more undulating links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

What has been needed and heretofore unavailable is a stent which has a high degree of flexibility so that it can be advanced through tortuous passageways and can be readily expanded, and yet have the mechanical strength to hold open the body lumen or artery into which it is implanted and provide adequate vessel wall coverage. The present invention satisfies this need. That is, the stent of the present invention has a high degree of compressibility to secure it on the catheter and provide a low profile and a high degree of flexibility making it possible to advance the stent easily through tortuous arteries, yet the stent has sufficient radial rigidity so that it can hold open an artery or other blood vessel, or tack up a dissected lining and provide adequate vessel wall coverage.

SUMMARY OF THE INVENTION

The present invention is directed to an intravascular stent that has a pattern or configuration that permits the stent to be tightly compressed or crimped onto a catheter to provide an extremely low profile and to prevent relative movement between the stent and the catheter. The stent also is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of cylindrical rings that are interconnected to form the stent. The stent typically is mounted on a balloon catheter if it is balloon expandable or mounted on or in a catheter without a balloon if it is self-expanding.

Each of the cylindrical rings making up the stent have a proximal end and a distal end and a cylindrical plane defined by a cylindrical outer wall surface that extends circumferentially between the proximal end and the distal end of the cylindrical ring. Generally the cylindrical rings have a serpentine or undulating shape which includes at least one U-shaped element, and typically each ring has more than one U-shaped element. The cylindrical rings are interconnected by at least one undulating link which attaches one cylindrical ring to an adjacent cylindrical ring. The undulating links are highly flexible and allow the stent to be highly flexible along its longitudinal axis. At least some of the undulating links have a curved portion that extends transverse to the stent longitudinal axis for a predetermined distance that coincides with one of the U-shaped elements. More specifically, the curved portion extends in a transverse manner such that it would intersect with the corresponding U-shaped element, however, the corresponding U-shaped element is shorter in length than other U-shaped elements in the same ring. Thus, when the stent is compressed or crimped onto the catheter, the curved portions do not overlap or intersect with the adjacent U-shaped element since that element is shorter in length than similar U-shaped elements in the particular ring. In this manner, the stent can be compressed or crimped to a much tighter or smaller diameter onto the catheter which permits low profile delivery as well as a tight gripping force on the catheter to reduce the likelihood of movement between the stent and the catheter during delivery and prior to implanting the stent in the vessel.

The undulating links may take various configurations but in general have an undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend and tip outwardly as the stent is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating links is positioned within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The undulating links are positioned so that the curved portion of the link is outside the curved part of the W-shaped portion. Since the curved portion does not substantially expand (if at all) when the stent is expanded, it will continue to provide good vessel wall coverage even as the curved part of the W-shaped portion spreads apart as the stent is expanded. The curved portion of the link extends in a direction transverse to the stent longitudinal axis for a distance that positions it adjacent and proximal to the peak of a U-shaped element. These U-shaped elements have struts that are shorter than the struts of the other U-shaped elements in the same cylindrical ring so that as the stent is compressed the curved portion of the link does not overlap the adjacent U-shaped element.

In one embodiment, the W-shaped portion has a first and second radius at its base where the first radius is greater than the second radius so that the first radius expands more easily than the second radius when the stent is expanded. The first radius corresponds with a second peak (U-shaped member) which is shorter than the other peaks in the ring. The second peak has shorter struts than the struts of the other peaks and as a result expands more slowly when the stent expands. Thus, faster expansion rate of the first radius of the W-shaped portion has a tendency to compensate for the slower expansion rate of the adjacent shorter second peak to provide overall uniform expansion of the stent. Also, the shorter second peak can have a greater radius than the longer first peaks, again to provide different expansion rates to obtain more uniform stent expansion.

In another embodiment, each ring has nine peaks, three each of first, second, and third peaks. The third peak has the longest struts, the second peak the shortest struts, and the first peak has intermediate length struts. In order to obtain uniform stent expansion, the radius of the peaks is inversely proportional to the strut length. The shorter second peak with the shortest struts has the biggest peak radius, the first peak has an intermediate radius, and the third peak with the longest struts has the smallest peak radius.

The number and location of undulating links that interconnect adjacent cylindrical rings can be varied as the application requires. Since the undulating links typically do not expand when the cylindrical rings of the stent expand radially outwardly, the links are free to continue to provide flexibility and to also provide a scaffolding function to assist in holding open the artery. Importantly, the addition or removal of the undulating links has very little impact on the overall longitudinal flexibility of the stent. Each undulating link is configured so that it promotes flexibility whereas some prior art connectors actually reduce flexibility of the stent.

The cylindrical rings of the stent are plastically deformed when expanded when the stent is made from a metal that is balloon expandable. Typically, the balloon-expandable stent is made from a stainless steel alloy or similar material.

Similarly, the cylindrical rings of the stent expand radially outwardly when the stent is formed from superelastic alloys, such as nickel-titanium (NiTi) alloys. In the case of superelastic alloys, the stent expands upon application of a temperature change or when a stress is relieved, as in the case of a pseudoelastic phase change.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention undulating links reduce the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

BRIEF DESCRIPTION OF THE DRAWINGS

FIG. 1 is an elevational view, partially in section, of a prior art stent mounted on a rapid-exchange delivery catheter and positioned within an artery.

FIG. 2 is an elevational view, partially in section, similar to that shown in FIG. 1 wherein the prior art stent is expanded within the artery, so that the stent embeds within the arterial wall.

FIG. 3 is an elevational view, partially in section, showing the expanded prior art stent implanted within the artery after withdrawal of the rapid-exchange delivery catheter.

FIG. 12 is a plan view of the stent of FIG. 10A rolled into a cylindrical configuration and in a crimped or compressed configuration.

FIG. 13 is a plan view of the stent of FIG. 10A in a cylindrical configuration and illustrating the rings and links in an expanded configuration.

DETAILED DESCRIPTION OF THE PREFERRED EMBODIMENTS

Figure 4:
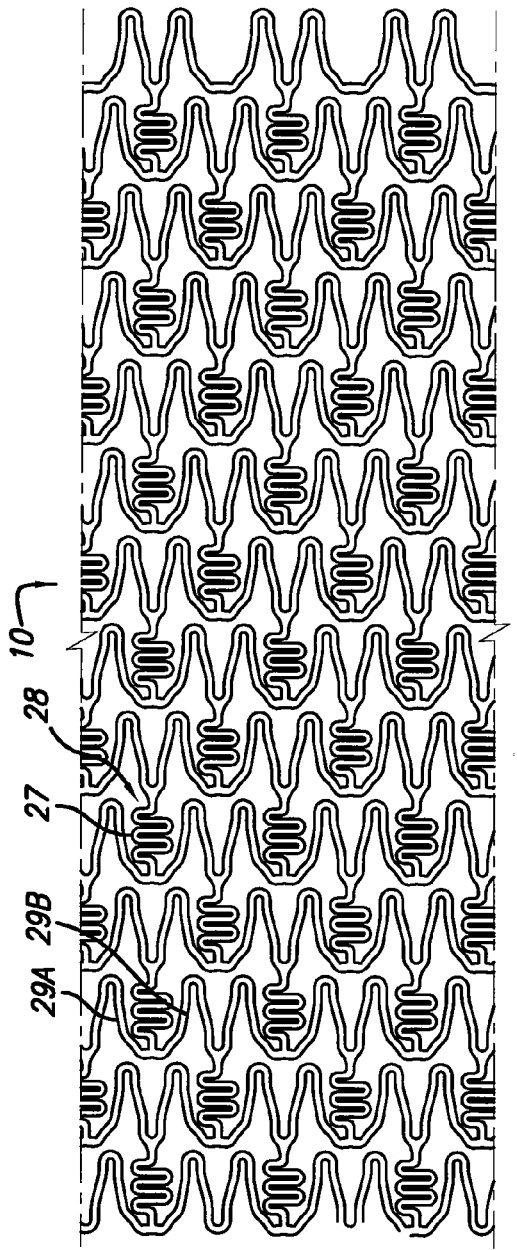
FIG. 4 is a plan view of a flattened prior art stent which illustrates the pattern of the stent shown in FIGS. 1-3.
Figure 5:
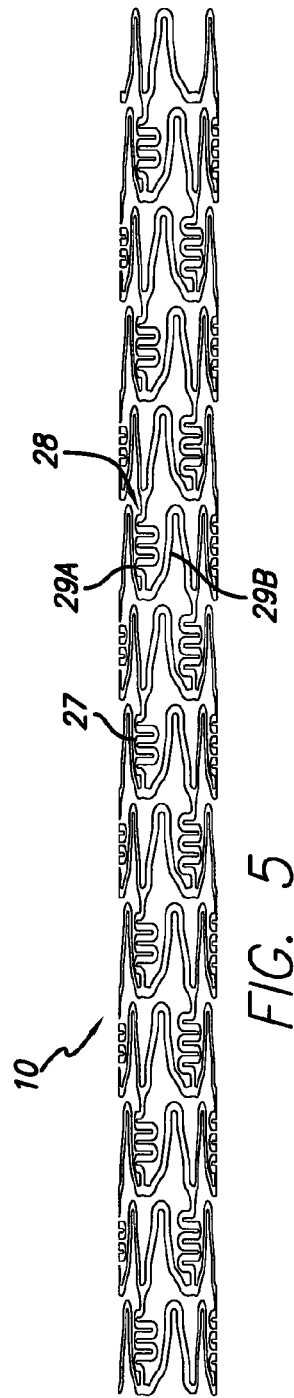
FIG. 5 is a side view of the prior art stent of FIG. 4 in a cylindrical configuration and in an unexpanded state.
Figure 6A:
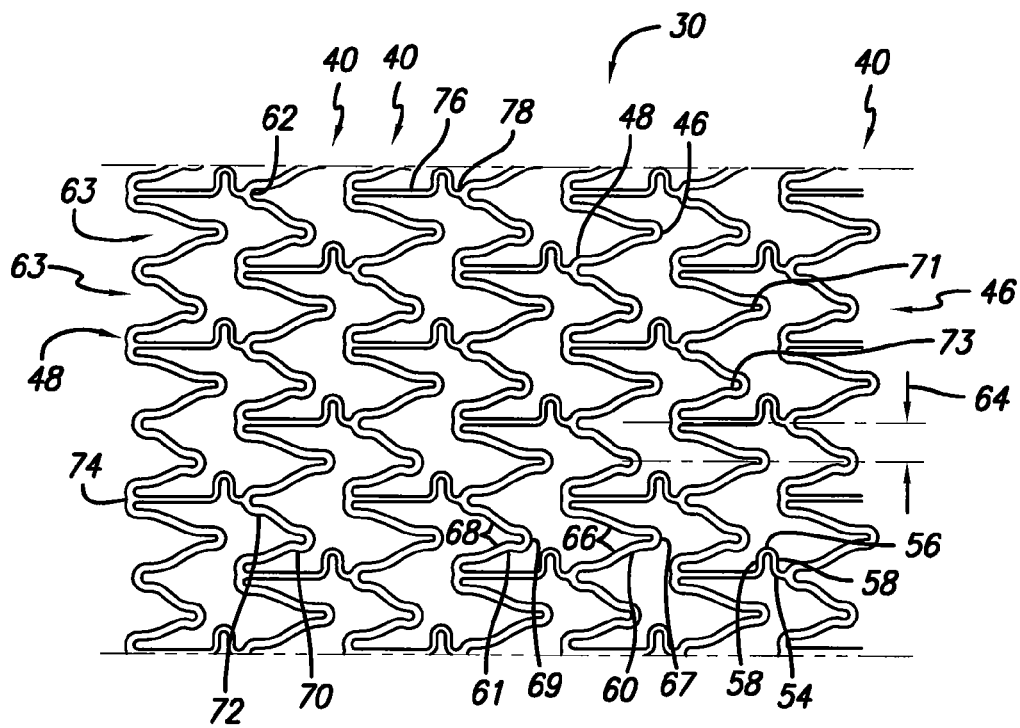
FIG. 6A is a plan view of a flattened stent of one embodiment of the invention which illustrates the pattern of the rings and links.
Figure 6B:
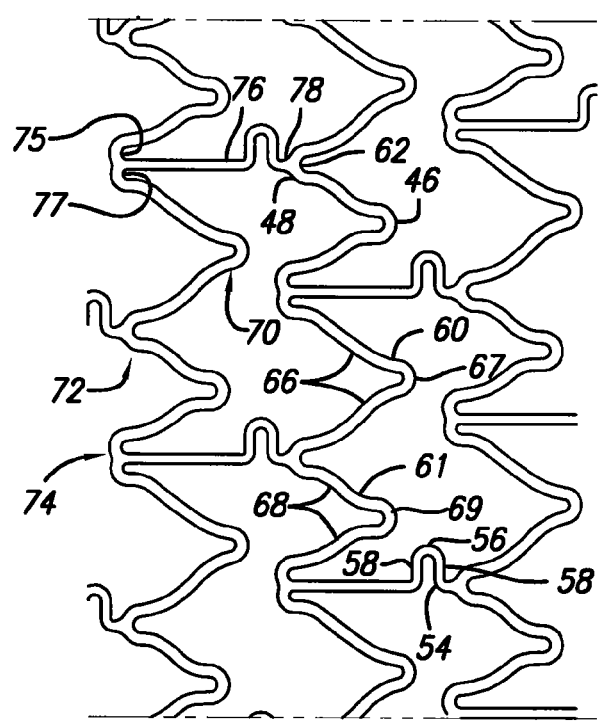
FIG. 6B is a partial plan view of the stent of FIG. 6A which has been expanded to approximately 3.0 mm inside diameter.
Figure 6C:
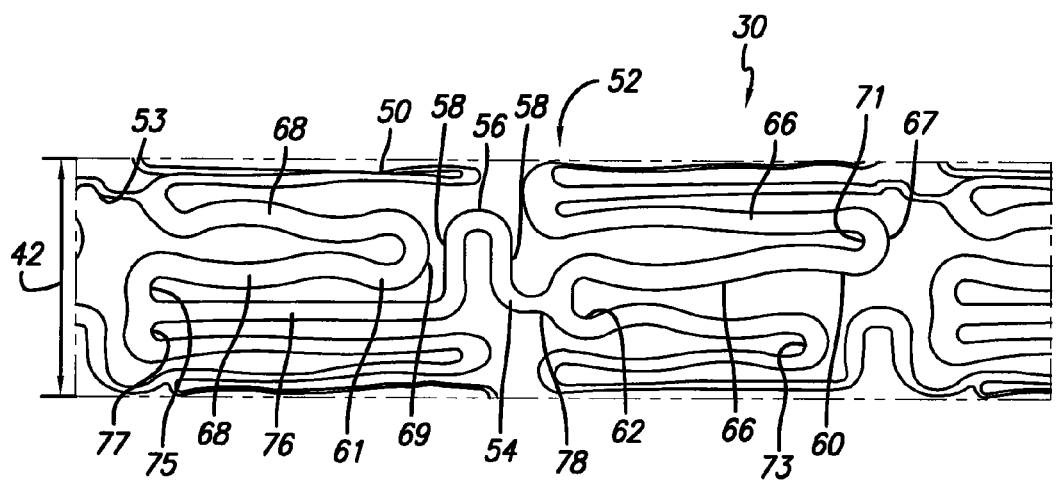
FIG. 6C is a plan view of a portion of the stent of FIG. 6A rolled into a cylindrical configuration and tightly crimped so that the various stent struts are either in close contact or contacting each other.
Figure 7A:
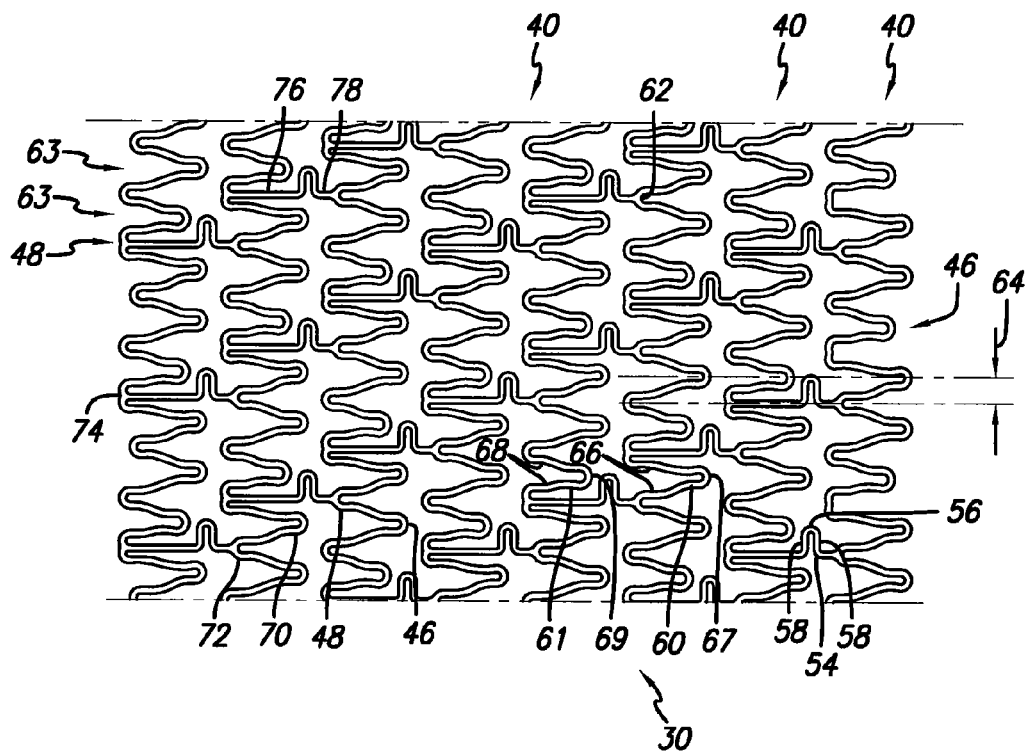
FIG. 7A is a plan view of a flattened stent of another embodiment of the invention which illustrates the pattern of the rings and links.
Figure 7B:
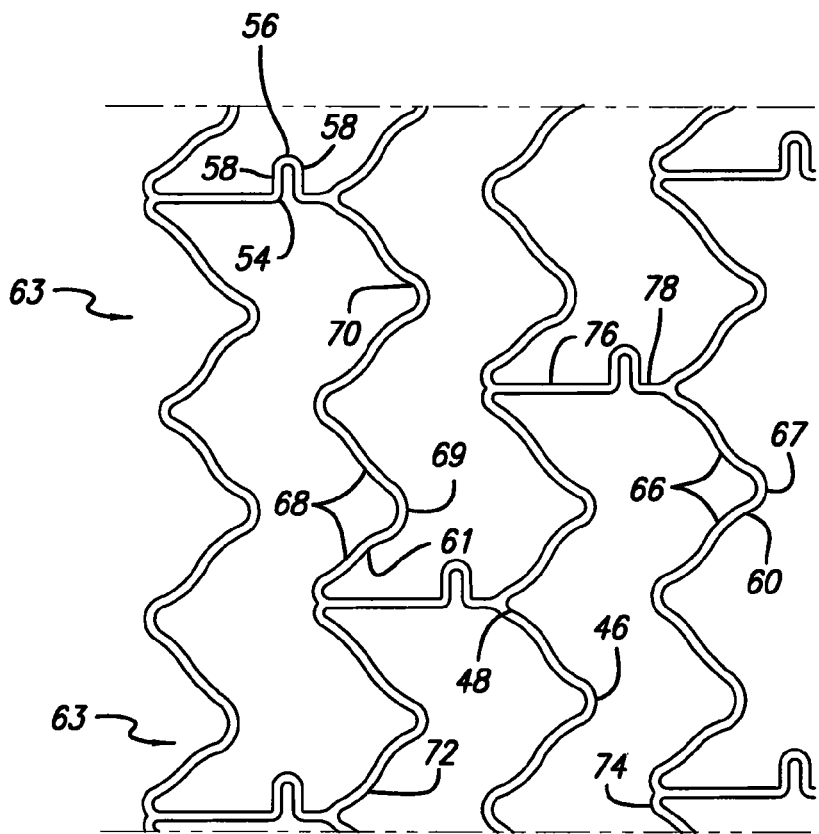
FIG. 7B is a partial plan view of the stent of FIG. 7A which has been expanded to approximately 4.0 mm inside diameter.
Figure 7C:
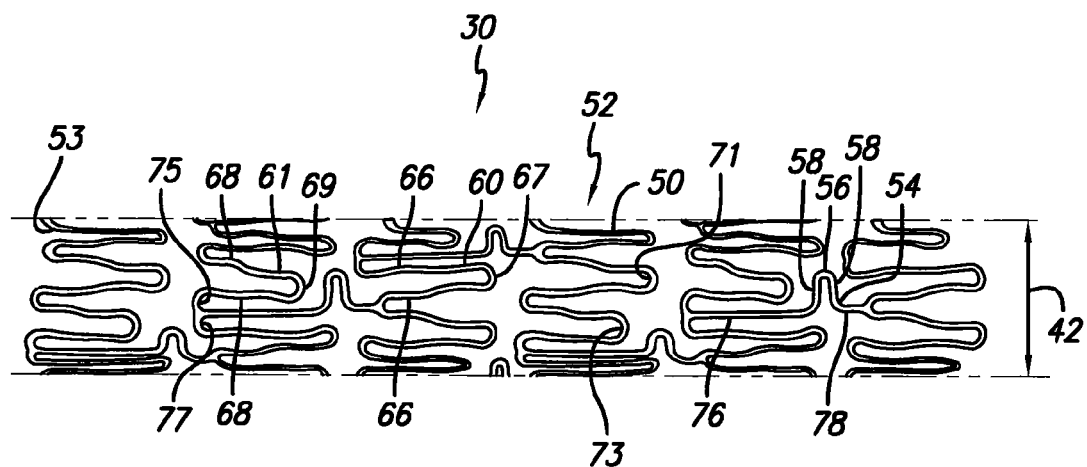
FIG. 7C is a portion of the stent of FIG. 7A that is illustrated in a cylindrical configuration and is tightly crimped or compressed.
Figure 8A:
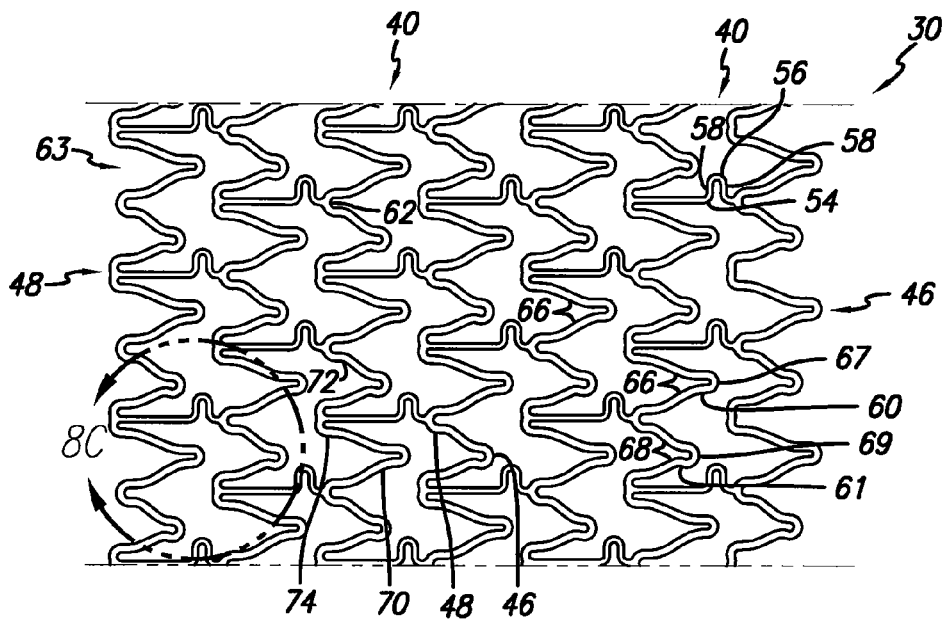
FIG. 8A is a plan view of a flattened stent of another embodiment of the invention which illustrates the pattern of the rings and links.
Figure 8B:
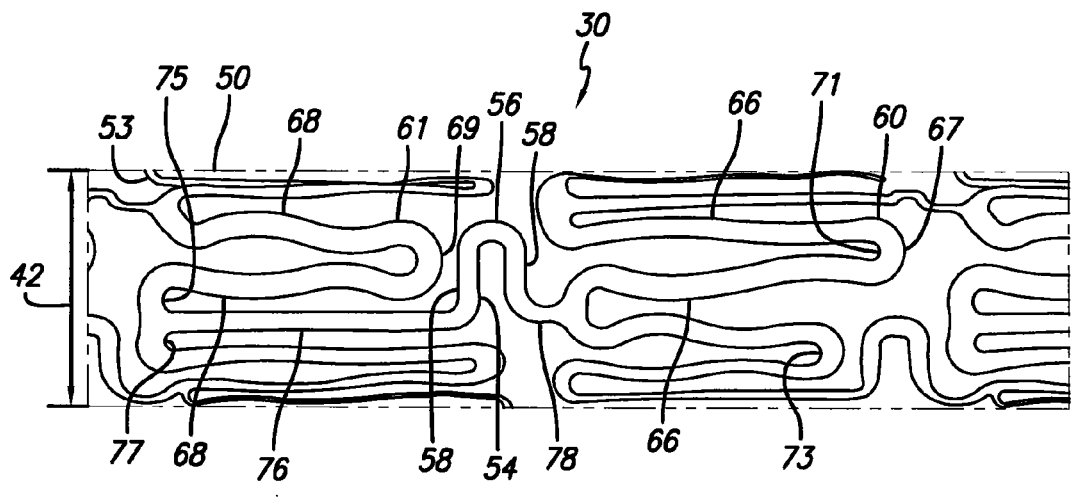
FIG. 8B is a plan view of the flattened stent of FIG. 8A where the rings and links have been crimped or tightly compressed.
Figure 8C:
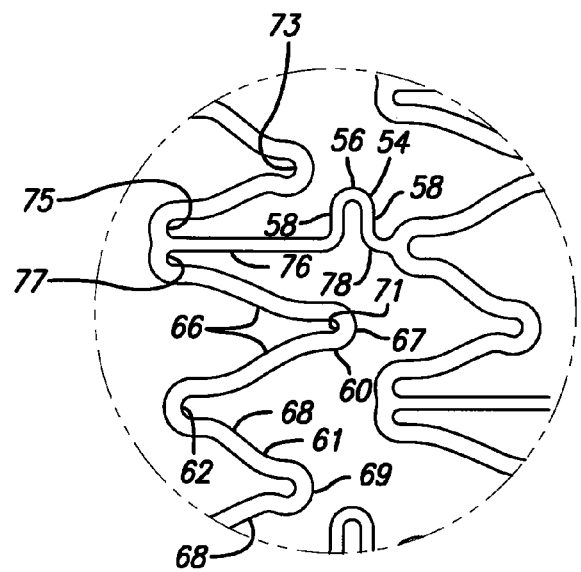
FIG. 8C is a plan view of a portion of the flattened stent of FIG. 8A illustrating the relationship of the U-shaped member to the undulating link prior to crimping the stent.
Figure 9A:
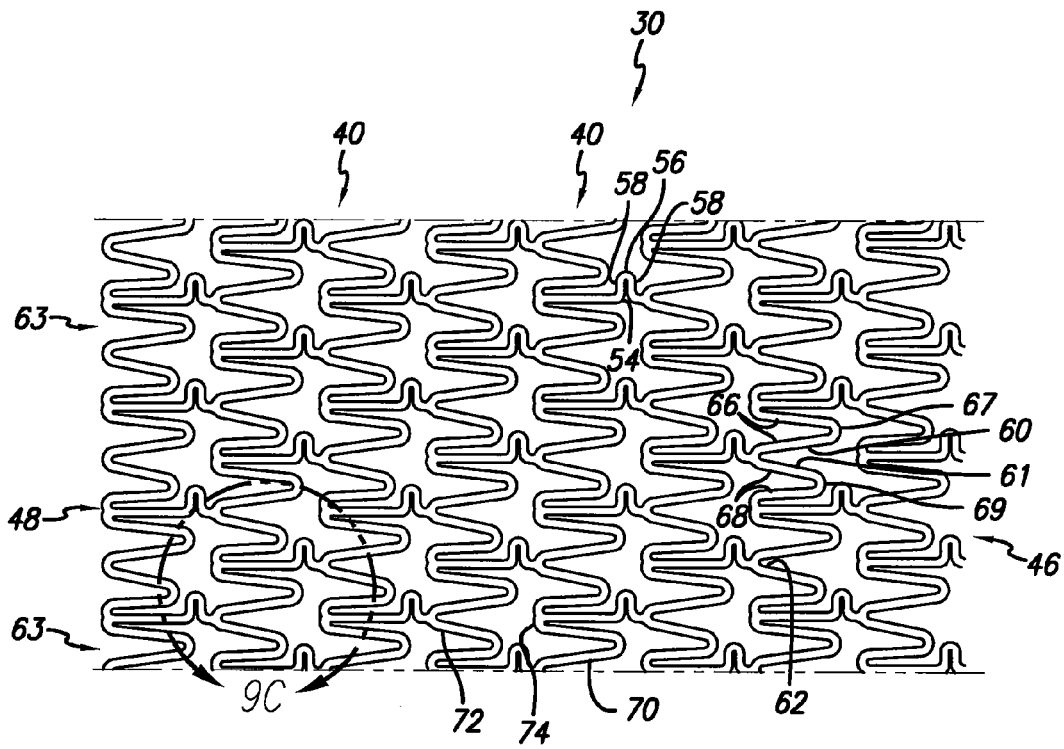
FIG. 9A is a plan view of a flattened stent of another embodiment of the invention which illustrates the pattern of the rings and links.
Figure 9B:
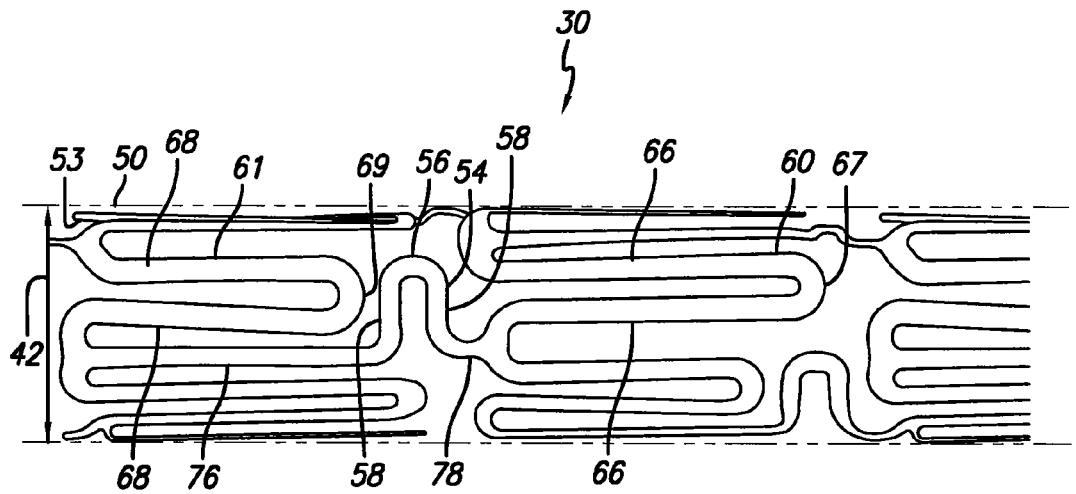
FIG. 9B is a plan view of the flattened stent of FIG. 9A where the rings and links have been crimped or tightly compressed.
Figure 9C:
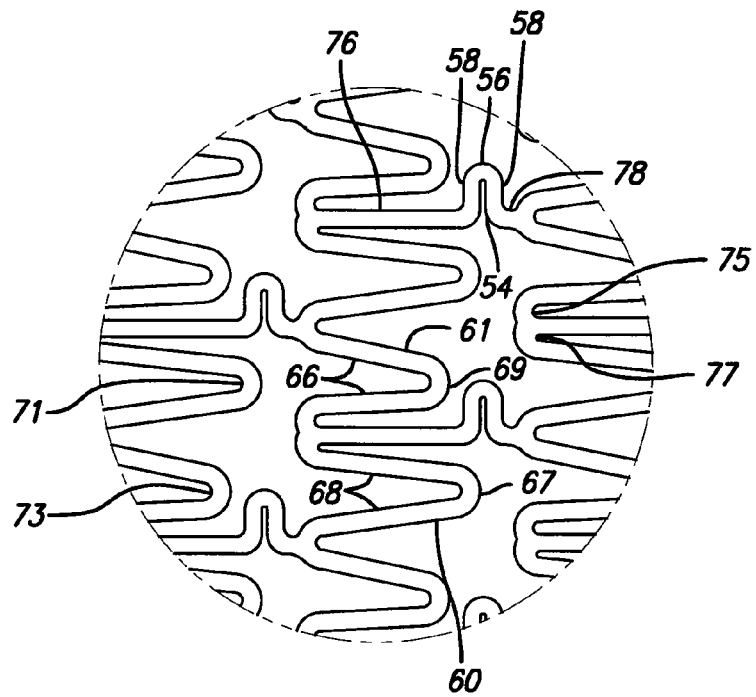
FIG. 9C is a portion of the flattened stent of FIG. 9A illustrating the relationship of the shortened U-shaped member and the undulating portion of the link when the stent is in a partially crimped or compressed configuration.
Figure 10A:
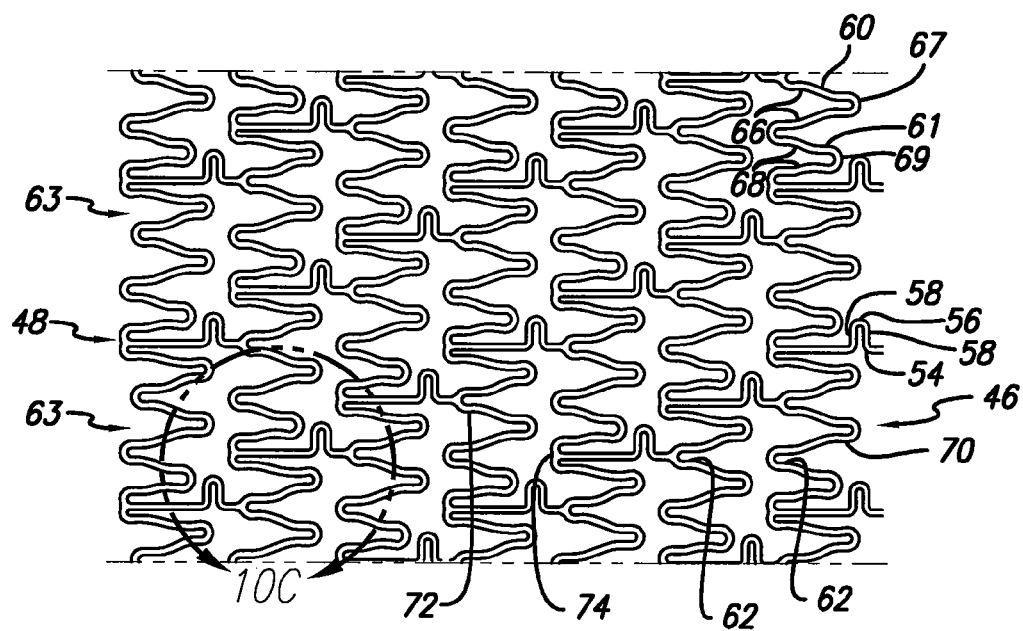
FIG. 10A is a plan view of a flattened stent of another embodiment of the invention which illustrates the pattern of the rings and links.
Figure 10B:
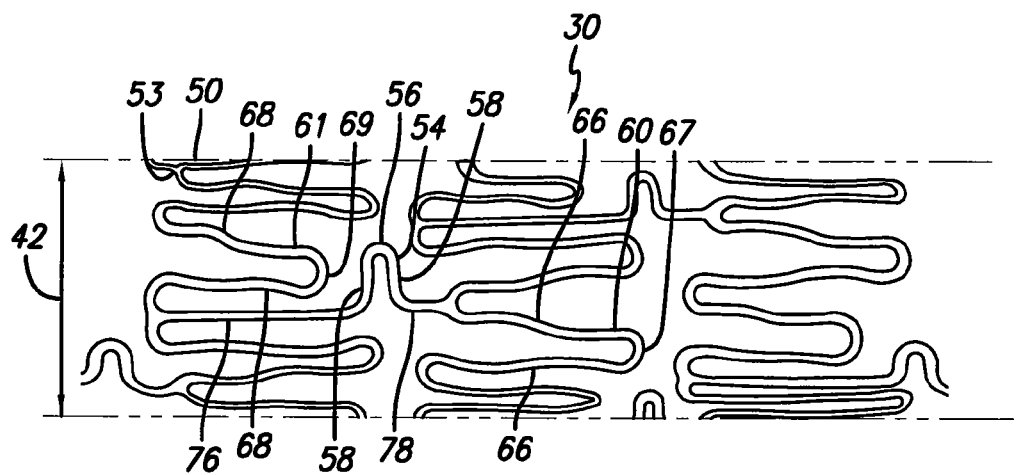
FIG. 10B is a plan view of the flattened stent of FIG. 10A in a crimped or compressed configuration.
Figure 10C:
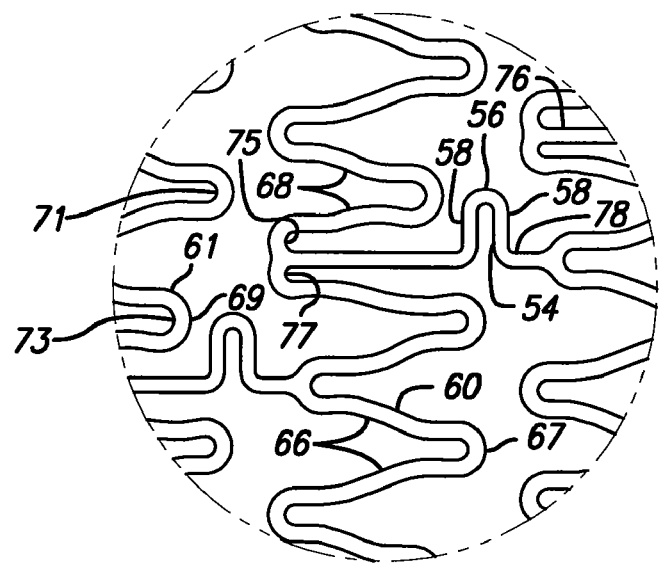
FIG. 10C is a partial plan view of the flattened stent of FIG. 10A depicting the relationship between the shortened U-shaped member and the undulating portion of the link when the stent is partially crimped or compressed.

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall, such as a coronary artery. The design of the highly flexible interconnecting members and their placement relative to an adjacent U-shaped member provides for a tightly compressed stent onto a catheter while maintaining a high degree of flexibility during delivery.

Turning to the drawings, FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

In a typical procedure to implant prior art stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the prior art stent expanded and pressed against the vessel wall, and in FIG. 3, the implanted stent remains in the vessel after the balloon has been deflated and the catheter assembly and guide wire have been withdrawn from the patient.

The prior art stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

One of the problems associated with some prior art stents such as the one shown in FIG. 4, is the ability to more tightly crimp or compress the stent 10 onto the balloon portion of the catheter. For example, the undulating portion 27 of the links 28 of the prior art stent in FIG. 4 are positioned between two struts 29A/29B so that as the stent is tightly crimped or compressed onto the balloon portion of the catheter, the struts can only come so close to the undulating portion before contact is made. Preferably, the undulating portion and the adjacent struts should not overlap, therefore the undulating portion of the link limits the amount of the crimping or compression of each cylindrical ring onto the balloon portion of the catheter. The present invention solves this problem and allows for a tightly compressed or crimped stent onto the catheter.

In keeping with the present invention, FIGS. 6-16 depict stent 30 in various configurations. Referring to FIG. 6A, for example stent 30 is shown in a flattened condition so that the pattern can be clearly viewed, even though the stent is in a cylindrical form in use, such as shown in FIG. 6C. The stent is typically formed from a tubular member, however, it can be formed from a flat sheet such as shown in FIG. 6A and rolled into a cylindrical configuration as shown in FIG. 6C.

As shown in FIGS. 6-16, stent 30 is made up of a plurality of cylindrical rings 40 which extend circumferentially around the stent when it is in a tubular form (see FIGS. 6C, 7C, 8B, 9B, 10B, 11B and 12). The stent has a delivery diameter 42 as shown in FIG. 12, and an implanted diameter 44 as shown in FIG. 13. Each cylindrical ring 40 has a cylindrical ring proximal end 46 and a cylindrical ring distal end 48. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 40 defines a cylindrical plane 50 which is a plane defined by the proximal and distal ends 46,48 of the ring and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

In keeping with the invention, undulating link 54 is positioned within cylindrical plane 50. The undulating links connect one cylindrical ring 30 to an adjacent cylindrical ring 30 and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

Referring to FIGS. 6-16, the stent 30 can be described more particularly as having a plurality of first peaks 60, second peaks 61, and valleys 62. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. As can be seen for example in FIG. 6A, peaks 60,61 are in phase 63, meaning that the peaks 60,61 point in the same direction and are substantially aligned along the longitudinal axis of the stent. It may be desirable under certain circumstances to position the peaks so that they are out of phase (not shown), that is, the peaks of one ring would be circumferentially offset from the peaks of an adjacent ring so that the apex of adjacent peaks pointed toward each other. As shown in FIGS. 6-16, the peaks are circumferentially offset 64 from the valleys and from the undulating link 54. Positioning the peaks, valleys, and undulating links in this manner, provides a stent having uniform expansion capabilities, high radial strength, a high degree of flexibility, and sufficient wall coverage to support the vessel.

In keeping with the invention, and as shown in FIGS. 6-16, each of the cylindrical rings has a plurality of first peaks 60 which have first struts 66 attached to a first apex 67. The first struts can be either curved or straight depending upon the particular application. The cylindrical rings also have second peaks 61 which have second struts 68 attached to a second apex 69. Again; the second struts can be either curved or straight depending upon the particular application. Importantly, the length of the second struts 68 are shorter than the length of the first struts 66. As can be seen in FIGS. 6C, 7C, 8B, 9A, 9B, 9C, 10A, 10B, 10C, 11A, 11B, 11C and 12, when the stent is in a crimped condition, or a partially crimped condition, the first struts and second struts respectively will be closer to each other when the stent is compressed or crimped onto the balloon or expandable member of the catheter. The crimping or compressing process, however, also moves the undulating link 54 along with its curved portion 56 closer to the second peak. In order to allow the stent to be more tightly crimped onto the balloon portion of the catheter, and to avoid overlapping between the undulating link and the second peak, the second struts 68 are shorter than the first struts 66, thus avoiding any overlapping contact between the curved portion of the undulating link and the second peak. The various stent struts, curved portions, links, and peaks and valleys may contact each other when the stent is crimped or compressed, but overlapping is an undesirable feature.

More particularly, in order to more tightly crimp or compress the cylindrical rings 40 of the stent 30, the undulating link 54 is tightly crimped or compressed into contact with, or near contact with, second peak 61. As can be seen, for example, in FIG. 6C, curved portion 56 and straight portions 58 are in close relation to second peak 61 and are either in contact (not shown) or near contact with second apex 69. The curved portion is proximal to the second peak and the various struts in each of the rings are tightly compressed to be in contact or near contact with each other. For example, first struts 56 and second struts 58 as well as arm 76 of the undulating link all are in close contact, or contact with each other in order to provide a very low profile, tightly crimped stent onto the balloon portion of the catheter. Likewise, if the stent is formed of a self-expanding material such as nickel-titanium, the stent will similarly be tightly crimped and positioned within a sheath or within the catheter for delivery in the vascular system. Importantly, the curved portion and the straight portions of the undulating link are positioned relative to the second peak to allow the stent to be tightly crimped as described.

As can be seen in FIGS. 6-16, there are slight variations in differing embodiments of the present invention. For example, the first struts 66 and the second struts 68 of the stent depicted in FIGS. 6A-6C, are curved and have several bends along their length. In contrast, as shown in FIGS. 9A-9C, the first struts and second struts are substantially straight. Whether the various struts are substantially straight or have slight bends is a matter of choice to suit a particular application.

Referring to FIGS. 6-16, the stent 30 of the invention also can be described as having cylindrical rings formed of U-shaped portions 70, Y-shaped portions 72, and W-shaped portions 74. Again, while the stent is generally laser cut from a tube and it typically has no discreet parts, for ease of identification the stent of the invention also can be referred to as having U-, Y-, and W-shaped portions. The U-shaped portions have no supporting structure attached thereto. The Y-shaped portions, at their base, or apex, have arm 78 extending therefrom which is attached to undulating link 54. The W portion has at its base or curve portion an arm 76 which attaches at the other end of the undulating link. The length of the arms attaching the links to the rings can vary.

Due to the intricate patterns as disclosed in FIGS. 6-13, the rate of expansion of the various portions of the stent, including the U-shaped portion 70, the Y-shaped portion 72, and the W-shaped portion 74, can vary. Accordingly, one aspect of the invention provides for different radii of curvature at various points so that the stent will expand evenly and uniformly. Thus, first radius 71 which corresponds with first peak 60 has a smaller radius of curvature than does second radius 72 which corresponds with second peak 61. Generally, the longer the struts associated with a peak, the more easily that portion of the stent will expand, so that a smaller radius is associated with peaks having longer struts. Likewise, for peaks, such as second peak 61, which has struts 68 that are shorter than the struts 66 of first peak 60, has a greater radius of curvature which will expand more easily in order to compensate for the stiffer bending moments created by the shorter struts 68.

Also referring to FIGS. 6-13, the radius of curvature of the various portions of the W-shaped portion also varies to provide uniform stent expansion. Since the second peak 61 and its associated struts 68 have a tendency to expand more slowly as the stent is expanded, a greater radius of a curvature is provided in the adjacent part of the W-shaped portion 74. Thus, third radius 75 of the W-shaped portion 74 is greater than the fourth radius 77 in the W-shaped portion. The third radius 75 is adjacent to second peak 61 which has a tendency to expand more slowly, while fourth radius 77 is adjacent the first peak 60 which has a tendency to expand more easily. By varying the radii of curvature in the W-shaped portion, the stent will expand more evenly and compensate for the varying rates of expansion of adjacent portions in a cylindrical ring.

Figure 11A:
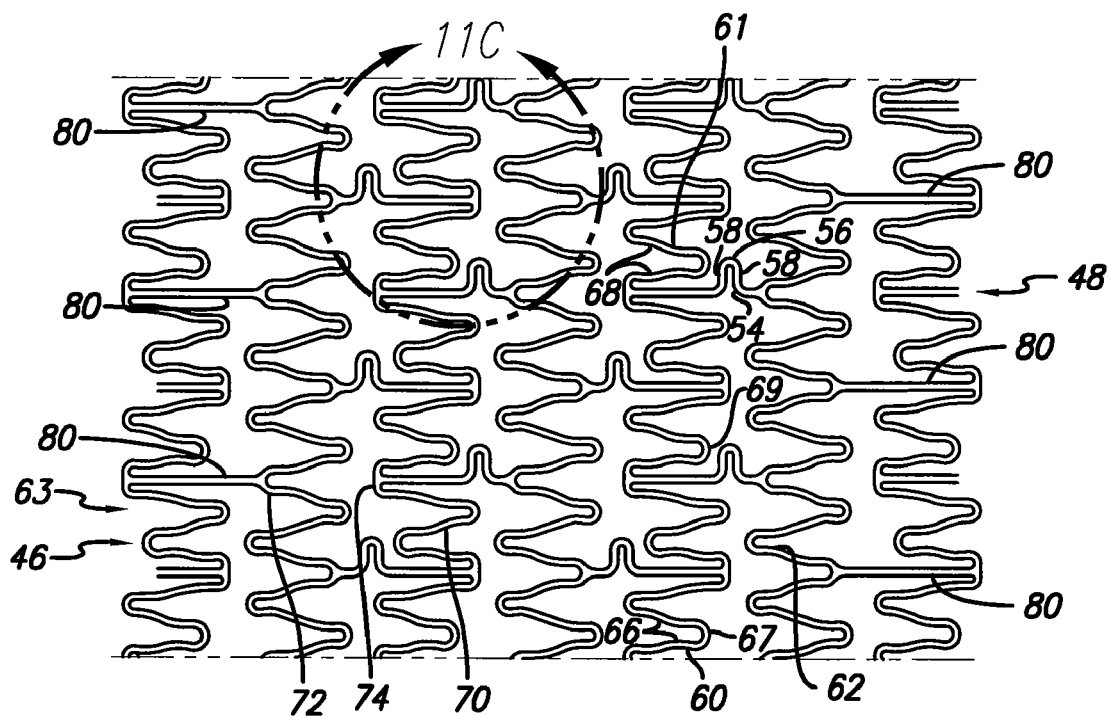
FIG. 11A is a plan view of a flattened stent of another embodiment of the invention which illustrates the pattern of the rings and links.
Figure 11B:
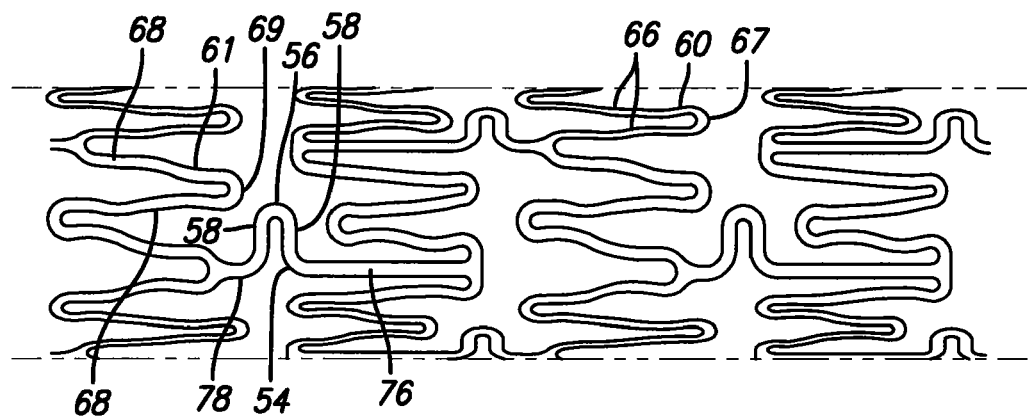
FIG. 11B is a plan view of the stent of FIG. 11A depicting the rings and links in a crimped or compressed configuration.
Figure 11C:
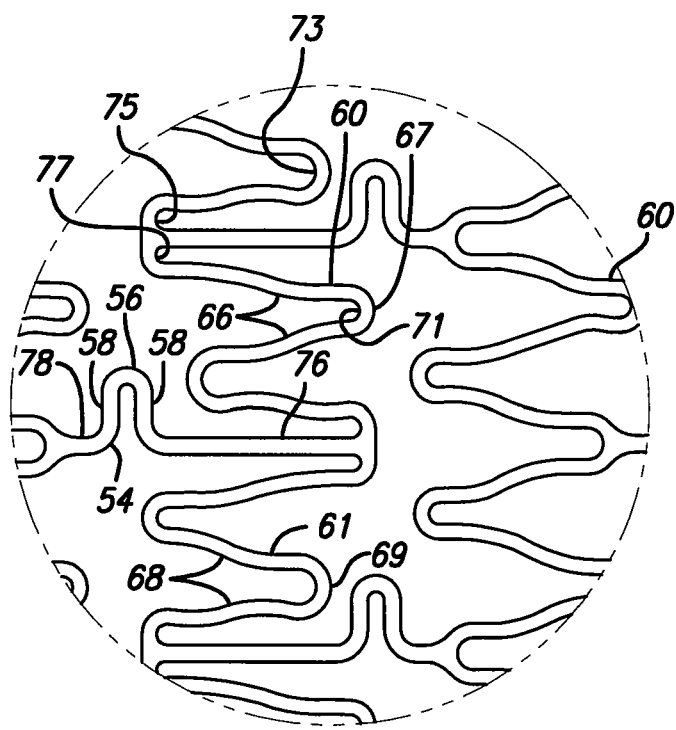
FIG. 11C is a partial plan view of the flattened stent of FIG. 11A depicting the relationship between the shortened U-shaped member and the undulating portion of the link when the stent is partially linked or compressed.

It is also a design feature that more or fewer undulating links 54 will be positioned between adjacent cylindrical rings 40. Further, in order to increase stent stability, straight links 80, as shown in FIG. 11A, in addition to undulating links 54, connect adjacent cylindrical rings. The straight links will provide stability and assist in preventing stent foreshortening, as do the undulating links. Further, the straight links may provide more rigidity in a localized area, such as at the stent ends, such that it may be desirable to incorporate more straight links between the cylindrical rings at the stent ends than in the center of the stent.

Figure 14:
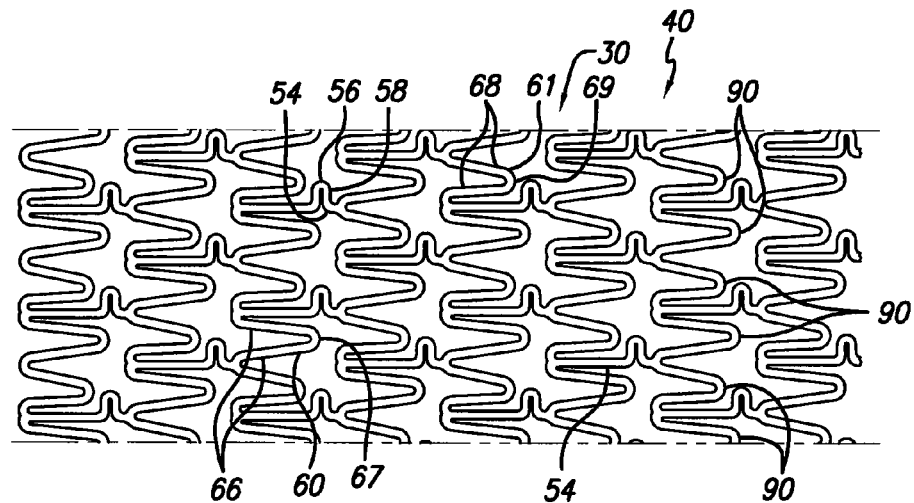
FIG. 14 is a plan view of a flattened stent of another embodiment of the invention which illustrates the pattern of rings and links.

In an alternative embodiment as shown in FIG. 14, stent 30 is designed to provide good vessel wall coverage and greater expandability since each cylindrical ring 40 has eight peaks 90. Generally, the more peaks in a cylindrical ring that has an undulating pattern, the greater the expansion capabilities of that particular ring. Further, the stent of FIG. 14 has a greater number of links 54 than in some of the other stent patterns. In this embodiment, there are four undulating links 54 between adjacent rings so that the stent has uniform flexibility and maintains sufficient vessel wall coverage.

Figure 15:
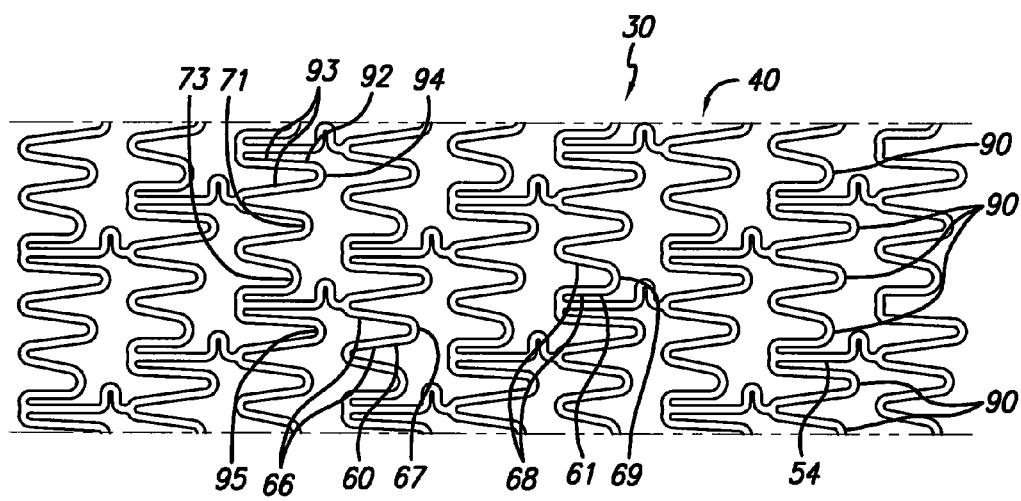
FIG. 15 is a plan view of a flattened stent of another embodiment of the invention which illustrates the pattern of the rings and links where each of the rings has nine peaks.

Referring to FIG. 15, an alternative embodiment of stent 30 is shown in which each cylindrical ring 40 has nine peaks 90. As with the stent pattern depicted in FIG. 14, the stent pattern of FIG. 15 is capable of expanding to a greater diameter due to the greater number of peaks 90 and yet maintain sufficient vessel wall coverage. In this embodiment, the first peak 60 and second peak 61 are substantially the same as previously described with respect to the stent patterns depicted in FIGS. 6-13. In this embodiment, however, a third peak 92 has a pair of third struts 93 and a third apex 94. Third peak 92 has third struts 93 that are longer than the first struts 66 and the second struts 68 of the first peak 60 and the second peak 61 respectively. As with the other embodiments, the struts 66 of the first peak 60 are longer than the second struts 68 of second peak 61. Further, in order to provide more uniform expansion of the stent, the third radius 95 of the third peak 92 is smaller than the first radius 71 of first peak 60. Likewise, as previously described, first radius 71 is smaller than second radius 73 of second peak 61. Generally speaking, the radius of curvature of the peaks are inversely proportional to the length of the struts so that the longer the struts the smaller the radius of curvature relative to shorter struts with a greater radius of curvature. As the stent expands, the peak having a greater radius of curvature will expand more easily than those having a smaller radius of curvature, thus, compensating for the length of the struts in which the peaks having shorter struts have a tendency to expand more slowly than peaks having longer struts and which have moment arms that bend more easily.

Figure 16:
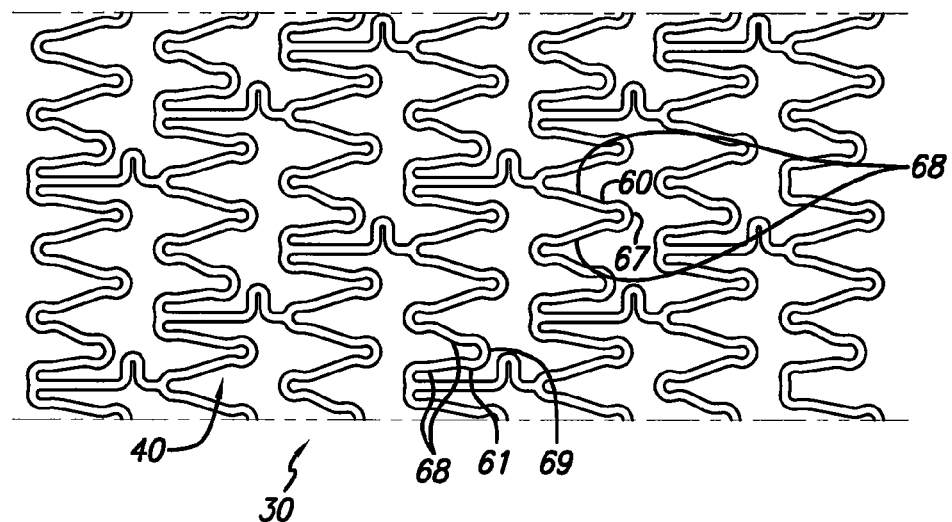
FIG. 16 is a plan view of a flattened stent of another embodiment of the invention which illustrates the pattern of the rings and links.

Referring to FIG. 16, the stent 30 is similar to the other embodiments except that the radius of curvature of all of the peaks and valleys are somewhat larger in order to make it easier to laser cut the stent pattern from a tubular member or from a flat sheet.

Figure 17:
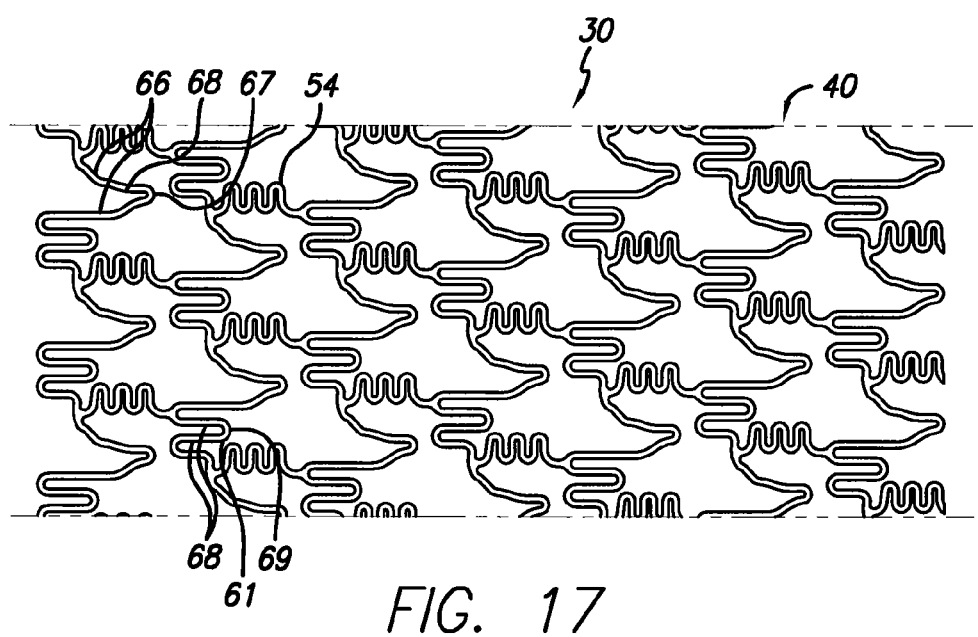
FIG. 17 is a plan view of a flattened stent depicting another embodiment of the invention which illustrates the pattern of rings and links.
Figure 18:
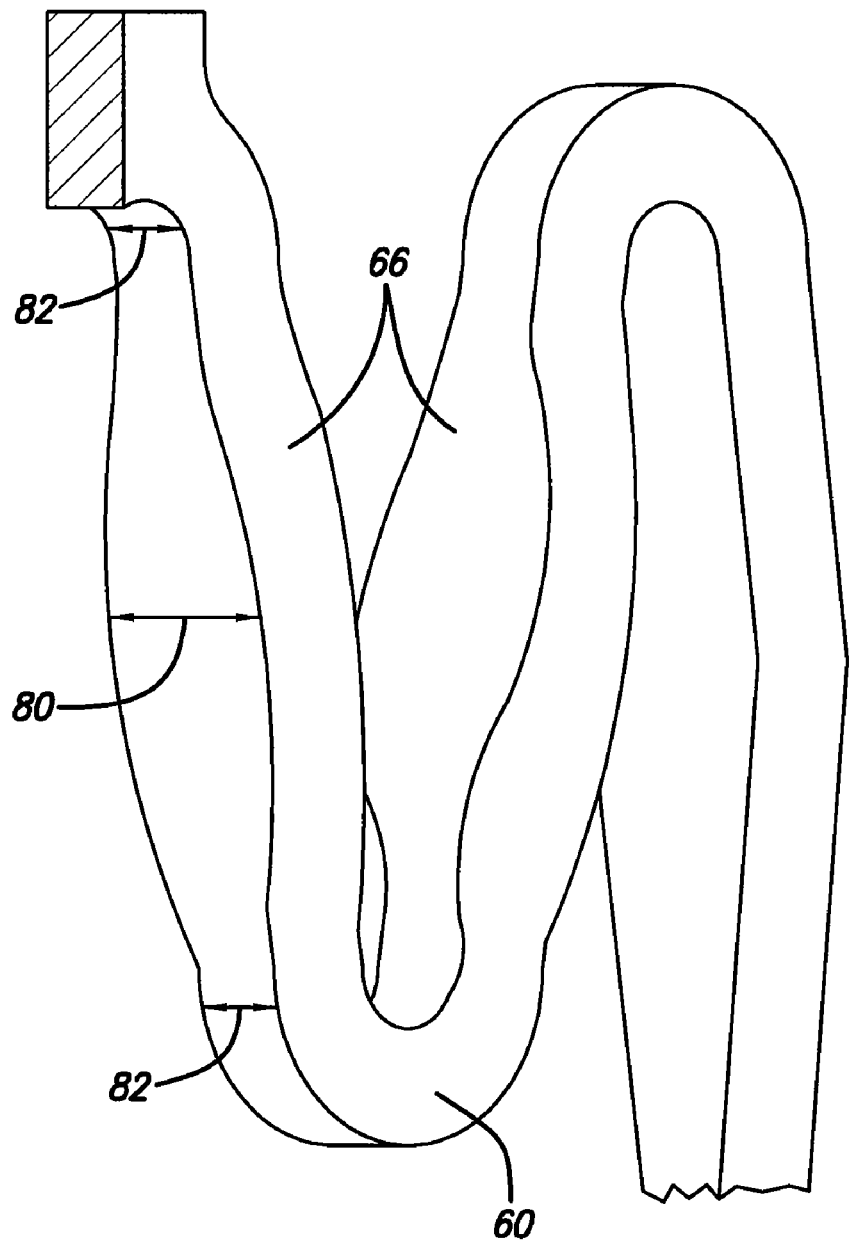
FIG. 18 is an enlarged partial perspective view of a portion of a peak and associated struts depicting variable thickness struts.

Turning to FIG. 17, in an alternative embodiment, the stent 30 includes a pattern that does not have a so-called W-shaped portion. In this embodiment, the undulating link 54 is substantially proximal to the second peak 61, with a slight portion of the undulating link 54 being circumferentially adjacent to the second peak. The first peak 60 still has struts 66 that are longer than struts 68 of second peak 61 so that the stent of this embodiment functions in substantially the same manner as that described for the other stent embodiments.

In one aspect of the invention, after stent 30 is implanted in a coronary artery, or other vessel, because of its novel design, the cylindrical rings 40 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

In another aspect of the invention, the stent 30 is formed so that the various struts of the cylindrical rings, including the U-shaped portions 70, Y-shaped portions 72, W-shaped portions 74, and the undulating links 54, all can be formed so that each has a variable thickness along the stent length. For example, the undulating link, and its associated arms 76,78 may be thicker at one end (arm 76) than at the other end of the link (arm 78). Further, first struts 66 and second struts 68 may vary in thickness (radial thickness) along their length in order to create variable flexibility in the rings. As shown in FIG. 16, first peak 60 has first struts 66 that have radial thick portion 80 in the middle of the struts and radial thin portion 82 near the ends of the struts. As another example, the rings at for example the proximal end of the stent may be thicker radially than the rings in the center of the stent. A variable thickness stent that would benefit from the present invention is described and disclosed in U.S. Ser. No. 09/343,962 filed Jun. 30, 1999 and entitled VARIABLE THICKNESS STENT AND METHOD OF MANUFACTURE THEREOF, which is incorporated herein in its entirety by reference thereto. A variable thickness stent would benefit from the flexible nature of the present invention stent and still be crimped to a very low profile delivery diameter due to the novel relationship between the second peak 61 and the undulating link 54.

The stent 30 of the present invention can be mounted on a balloon catheter similar to that shown in the prior art device in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

The stent 30 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum. In accordance with the invention, it is preferred to cut the tubing in the desired pattern by means of a machine-controlled laser as is well known in the art.

The tubing may be made of suitable biocompatible material such as stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00-19.00% |
| Nickel (Ni) | 13.00-15.50% |
| Molybdenum (Mo) | 2.00-3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is mounted in a rotatable collet fixture of a machine-controlled apparatus for positioning the tubing relative to a laser. According to machine-encoded instructions, the tubing is rotated and moved longitudinally relative to the laser which is also machine controlled. The laser selectively removes the material from the tubing by ablation and a pattern is cut into the tube, The tube is therefore cut into the discrete pattern of the finished stent.

The process of cutting a pattern for the stent into the tubing is automated except for loading and unloading the length of tubing. In one example, a CNC-opposing collet fixture for axial rotation of the length of tubing is used in conjunction with a CNC X/Y table to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (0.005 to 0.001 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made typically of stainless steel with an outside diameter in the range of about 0.060 inch to 0.070 inch and a wall thickness in the range of about 0.002 inch to 0.005 inch. These tubes are fixtured under a laser and positioned utilizing a CNC to generate a very intricate and precise pattern. Due to the thin wall and the small geometry of the stent pattern (about 0.0035 inch typical web width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd—YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leqq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCl for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCl for 1-4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structure are rinsed in water. They are now ready for electropolishing.

The stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110°-135° F. and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. The struts have generally perpendicular edges formed by the laser cut. The resulting stent structure provides superior performance.

Other methods of forming the stent of the present invention can be used, such as using different types of lasers; chemical etching; electric discharge machining; laser cutting a flat sheet and rolling it into a cylinder, and the like, all of which are well known in the art at this time.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of undulations or U-shaped portions per ring, materials used, and the like have been described herein and are provided as examples only. Other modifications and improvements may be made without departing from the scope of the invention.

What is claimed is:

1. A flexible intravascular stent for use in a body lumen, comprising:

a plurality of cylindrical rings aligned along a common longitudinal axis and interconnected to form the stent, at least one cylindrical ring having a first delivery diameter and a second implanted diameter;

each cylindrical ring having a plurality of first peaks, each of the first peaks having a first height;

each cylindrical ring having a plurality of second peaks, each second peak having a second height, the second height being shorter than the first height;

at least one undulating link attaching at least one cylindrical ring to an adjacent cylindrical ring, the undulating links having a curved portion extending transverse to the stent longitudinal axis toward the second peak, the second height of the second peak being sized so that as the stent is compressed to the first delivery diameter, the curved portion of the undulating link is longitudinally aligned with the second peak and no portion of the undulating link contacts the second peak, the first height of the first peak being sized so as to be circumferentially aligned with at least a portion of said curved portion of said undulating link; and each undulating link having a first arm that is straight and substantially parallel to the longitudinal axis, and a second curved arm.

2. The stent of claim 1, wherein the first arm has a length extending along said stent and the second curved arm has a length extending along said stent, the length of the first arm being substantially greater than the length of the second curved arm.

3. The stent of claim 1, wherein the curved arm has a first end attached to a base of a Y-shaped element.

4. The stent of claim 3, wherein the second curved arm has a second end attached to a straight portion of the undulating link.

5. The stent of claim 1, wherein the second curved arm is longitudinally flexible.

6. The stent of claim 1, wherein the second curved arm does not expand longitudinally when the stent is expanded from the first delivery diameter to the second implanted diameter.

7. The stent of claim 1, wherein the stent has selected adjacent cylindrical rings that are connected to one another by at least one substantially straight link.

8. The stent of claim 7, the selected adjacent cylindrical rings are connected to one another by three substantially straight links.

9. The stent of claim 8, the substantially straight links are less flexible longitudinally than are the undulating links.

\* \* \* \* \*